US007783334B2

(12) United States Patent
Nam et al.

(10) Patent No.: US 7,783,334 B2
(45) Date of Patent: Aug. 24, 2010

(54) GARMENT FOR MEASURING PHYSIOLOGICAL SIGNAL

(75) Inventors: Seung Hoon Nam, Daejeon (KR); Seung Hwan Kim, Daejeon (KR); Kyung Hi Hong, Daejeon (KR); Hye Jun Park, Daejeon (KR)

(73) Assignees: Electronics and Telecommunications Research Institute, Daejeon (KR); The Industry & Academic Corporation in Chungnam National University, Daejeon (KR)

( * ) Notice: Subject to any disclaimer, the term of this patent is extended or adjusted under 35 U.S.C. 154(b) by 1082 days.

(21) Appl. No.: 11/481,611

(22) Filed: Jul. 6, 2006

(65) Prior Publication Data

US 2007/0038057 A1   Feb. 15, 2007

(30) Foreign Application Priority Data

Dec. 8, 2005   (KR) .................... 10-2005-0119297
Feb. 25, 2006   (KR) .................... 10-2006-0018511

(51) Int. Cl.
*A61B 5/04* (2006.01)
(52) U.S. Cl. ..................................... 600/388
(58) Field of Classification Search .......... 600/386, 600/388, 389, 393
See application file for complete search history.

(56) References Cited

U.S. PATENT DOCUMENTS

| 4,583,547 | A   |     | 4/1986  | Granek et al.          |
|-----------|-----|-----|---------|------------------------|
| 6,668,380 | B2  |     | 12/2003 | Marmaropoulos et al.   |
| 6,687,523 | B1  | *   | 2/2004  | Jayaramen et al. ...... 600/388 |
| 7,324,841 | B2  | *   | 1/2008  | Reho et al. ............ 600/382 |
| 7,395,106 | B2  | *   | 7/2008  | Ryu et al. ............. 600/388 |
| 2006/0211937 | A1 | * | 9/2006  | Eldridge ............... 600/388 |

FOREIGN PATENT DOCUMENTS

| KR | 1020050003435 | 1/2005  |
| WO | WO 89/02246   | 3/1989  |
| WO | WO 03/094717  | 11/2003 |
| WO | WO 03/095020  | 11/2003 |
| WO | WO 2004/058346 | 7/2004 |

* cited by examiner

*Primary Examiner*—Lee S Cohen
(74) *Attorney, Agent, or Firm*—Ladas & Parry LLP

(57) ABSTRACT

Provided is a smart garment for measuring a physiological signal which can improve comfort and convenience of wear and correctly measure a physiological signal. The smart garment for measuring physiological signals includes an electrode which is made of an electro-conductive fabric and detects a physiological signal, a physiological signal transmission line through which the detected physiological signal is transmitted, a physiological signal measuring unit which is connected to the transmission line, receives the physiological signal, and measures information regarding body conditions related to the physiological signal, and a pocket where the physiological signal measuring unit in inserted.

6 Claims, 6 Drawing Sheets

GARMENT FOR MEASURING PHYSIOLOGICAL SIGNAL

CROSS-REFERENCE TO RELATED PATENT APPLICATION

This application claims the benefit of Korean Patent Application No. 10-2005-0119297, filed on Dec. 8, 2005, and No. 10-2006-0018511, filed on Feb. 25, 2006, in the Korean Intellectual Property Office, the disclosure of which is incorporated herein in its entirety by reference.

BACKGROUND OF THE INVENTION

1. Field of the Invention

The present invention relates to a smart garment for measuring a physiological signal, and more particularly, to a smart garment which can improve the comfort and convenience of a user wearing it and correctly measure a physiological signal.

2. Description of the Related Art

Recently, with the increase in the number of health-conscious people, and as the number of senior citizens living alone is rising due to an increase in since an average life expectancy, a need for developing a health monitoring system has increased. Also, public demand for acquiring biometric information in real time is growing. Accordingly, methods of measuring a physiological signal in everyday life by inserting a sensor or module for measuring the physiological signal into a normal garment are developing.

The following are examples of conventional garments used to measure physiological signals. First, a garment includes a wearable electrode/sensor which is selectively detachable/attachable. Specifically, a HI-MEG of Velcro co., is used to allow the electrode/sensor to be easily detached/attached, and an electro-conductive silicon is disposed on the electrode for better contact with the skin of a user and to provide conductivity. However, the garment is inconvenient to use because the electrode has to be detached/attached when the physiological signals are measured.

Second, a middle portion of a garment is folded so that an electrode is fixed. However, the garment has drawbacks in that the electrode may drop or slide from the skin due to motion of the user when the physiological signals are measured, and thereby be unable to correctly measure the physiological signals.

Third, an elastic band is used so that an electrode is fixed. In this case, while wearing the garment, a user feels less comfortable.

The garments in the above cases are uncomfortable to wear as a normal garment and the measured physiological signals are highly affected by motion.

SUMMARY OF THE INVENTION

The present invention provides a smart garment which can maximize comfort and convenience of wear and can maintain quality of a physiological signal for a correct measurement of the physiological signal.

According to an aspect of the present invention, there is provided a smart garment for measuring physiological signals, comprising: an electrode which is made of an electro-conductive fabric and detects a physiological signal; a physiological signal transmission line through which the detected physiological signal is transmitted; a physiological signal measuring unit which is connected to the transmission line, receives the physiological signal, and measures information regarding body conditions related to the physiological signal; and a pocket where the physiological signal measuring unit is inserted.

In addition, an adhesive silicon may be coated around the electrode to reduce a contact resistance between the electrode and skin, so as to reduce noise generated when the electrode detects the physiological signal.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
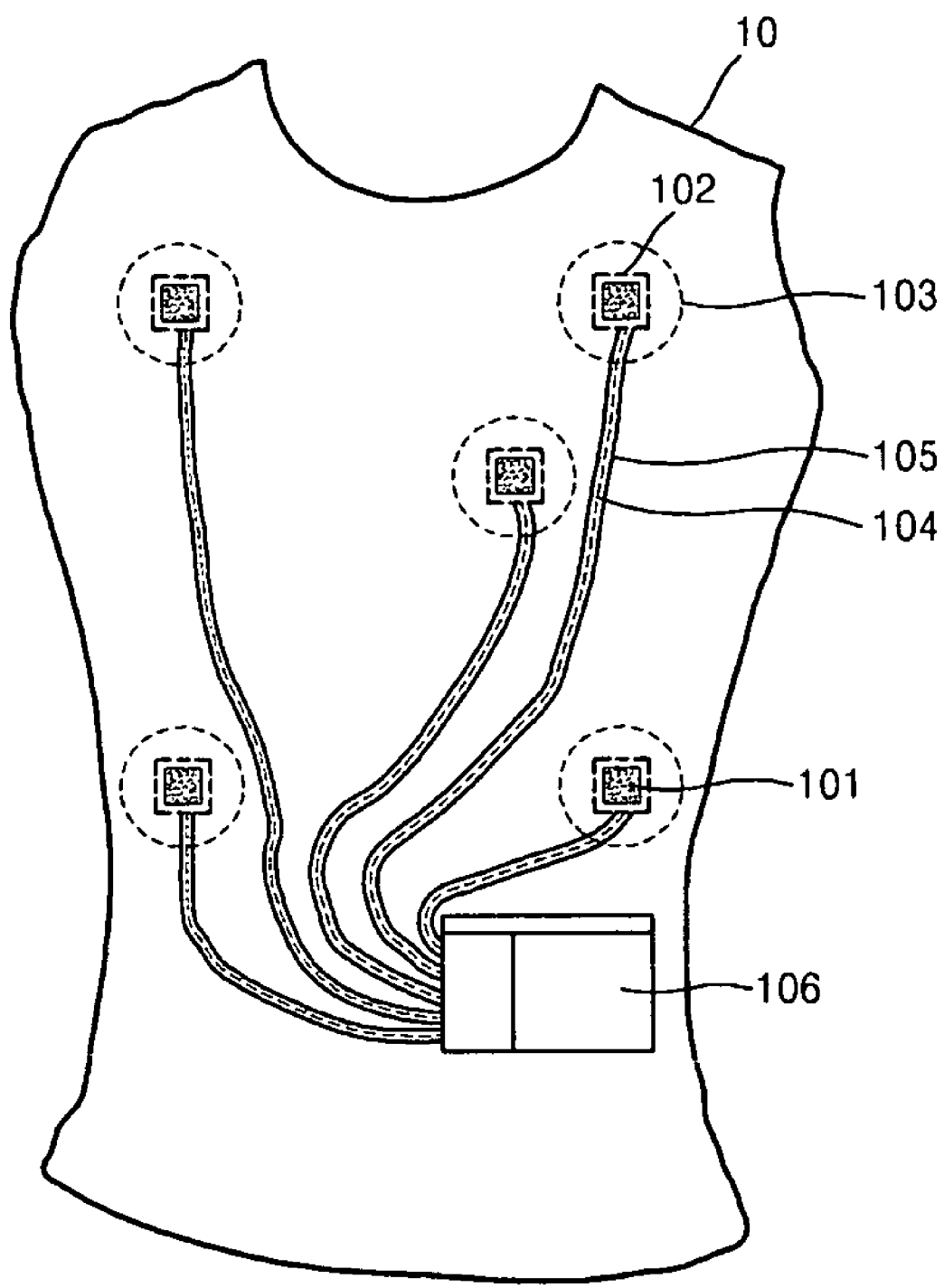
FIG. 1 is a front view of a smart garment for measuring a physiological signal according to an embodiment of the present invention.

For convenience, a technical feature of the present invention will be described in advance. In the present invention, an adhesive silicon is coated around a fabric electrode for detecting a physiological signal so that the electrode can strongly contact with skin and maintain a stable contact with the skin when a user dressed in a smart garment moves. Therefore, by reducing contact resistance between the skin and the electrode, a noise generated when the physiological signal is detected/monitored can be decreased.

The attached drawings for illustrating exemplary embodiments of the present invention are referred to so as to gain a sufficient understanding of the present invention, the merits thereof, and the objectives accomplished by the implementation of the present invention. Hereinafter, the present invention will be described in detail by explaining exemplary embodiments of the invention with reference to the attached drawings. Like reference numerals in the drawings denote like elements.

FIG. 1 is a front view of a smart garment for measuring a physiological signal according to an embodiment of the present invention.

A smart garment 10 includes an electrode 101 which detects a physiological signal, a adhesive silicon 103 which fixes the electrode 101 to skin so it does not drop from a skin surface, a transmission line 104 which transmits the physiological signal to a physiological signal measuring unit 30, a tuck 105 which insulates the transmission line 104 and fixes the transmission line 104 to the smart garment 10, and a pocket 106 which can contain the physiological signal measuring unit 30.

Figure 2A:
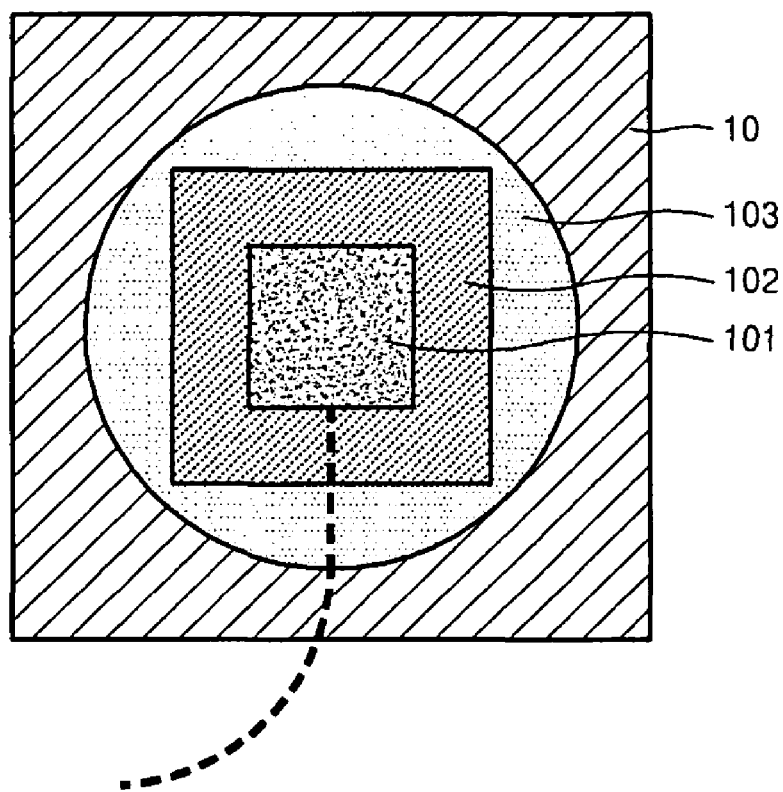
FIG. 2A is a cross-sectional view of an electrode of FIG. 1, which detects a physiological signal.
Figure 2B:
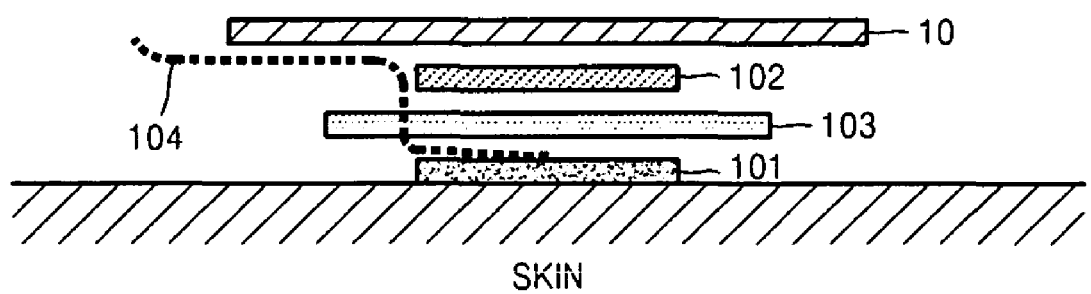
FIG. 2B is a horizontal cross-sectional view of the electrode of FIG. 2A.

FIG. 2A is a cross-sectional view of the electrode 101 which detects a physiological signal. FIG. 2B is a horizontal cross-sectional view of the electrode 101 of FIG. 2A.

The electrode 101 is made of an electro-conductive fabric to detect a physiological signal, is more pleasant to touch than a knitted electrode, and is washable. The electro-conductive fabric may be made of Ni/Cu polyester, Ni/Cu polyester taffeta, Ni/Cu nylon, or Ni/Cu polyester mesh. In addition, the electro-conductive fabric may be made of a thin layer such as tin, Ag/AgCl film, or stainless steel. Although an electrolyte gel is present in most electrodes for detecting physiological signals, in the present invention, a dry electrode is formed without using an electrolyte gel.

A cushion sheet 102 is disposed between the garment 10 and the electrode 101, and is pressed by the garment 10 and the electrode 101, so that the electrode 101 can tightly contact skin.

The adhesive silicon 103 is coated around the electrode 101 approximately with a size of 10~20 mm and a width of 0.5~1 mm. Thus, the electrode 101 can be strongly attached to the skin surface, and thus the electrode 101 is less likely to drop or slide from the skin surface when motion occurs. That is, by reducing a contact resistance between the skin surface and the electrode 101, noise generated when physiological signals are detected/monitored can be decreased.

Figure 3A:
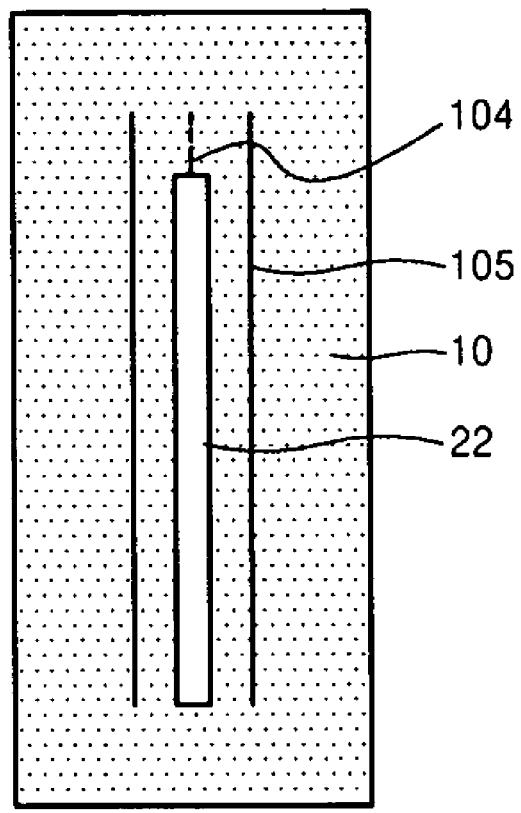
FIG. 3A is a front view of a tuck of FIG. 1 which insulates a physiological signal transmission line.
Figure 3B:
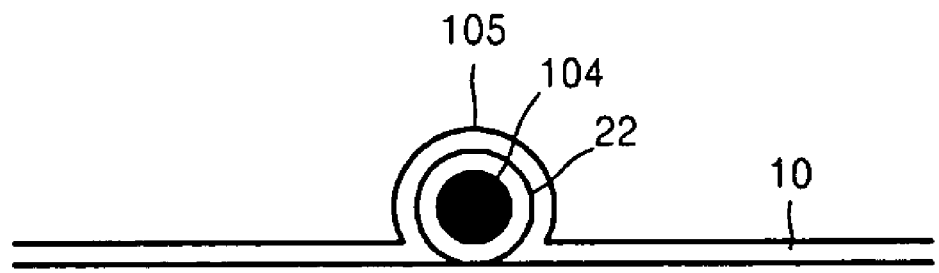
FIG. 3B is a cross-sectional view of the tuck of FIG. 3A.

FIG. 3A is a front view of a tuck which insulates a physiological signal transmission line. FIG. 3B is a cross-sectional view of the tuck of FIG. 3A.

The tuck 105 is formed by folding and sewing a garment 10 by around 2~4 mm. The transmission line 104 made of an electro-conductive thread is inserted into the tuck 105, and is insulated from outside in the form of a corded tuck. Since the tuck is sewn forming a curved line, the transmission line 104 inside the tuck can easily move along with the motion of the user without having to deform the shape of the garment 10.

The tuck 105 is formed such that the transmission line 104 can be disposed in any position in the garment 10. Although the tuck 105 is formed on a surface of the garment 10, and the transmission line 104 which transmits physiological signal data is inserted therein in the present embodiment, when the garment 10 is made of a non-elastic material, the transmission line 104 can be re-disposed after the surface of the garment 10 is glued with an adhesive fiber material 22 by using a heat-fusion tape or adhesive used for seam sealing.

Figure 4:
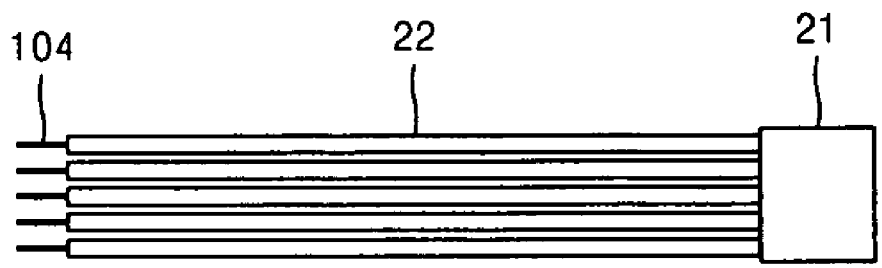
FIG. 4 is a plan view of a transmission line of FIG. 1 made of an electro-conductive thread, and a connector.

FIG. 4 is a plan view of the transmission line of FIG. 1 made of an electro-conductive thread, and a connector.

A physiological signal detected by the electrode 101 is transmitted to the physiological signal measuring unit 30 connected to a connecter 21 by the transmission line 104 made of an electro-conductive thread. The transmission line 104 is made of an electro-conductive thread VN 12/2x275/175S produced by BEKAERT Co., of Belgium. The thread is made of tens of threads using 100% pure stainless steel a few μm in diameter. Since the thread has an extremely small electrical resistance of 0.2 ohm/cm, the thread can be used for transmitting data. Although the electro-conductive thread VN 12/2x275/175S by BEKAERT is used in the present embodiment, the transmission line 104 may be made of other flexible electro-conductive threads.

In addition to the tuck 105, in order to insulate the electro-conductive line 104, a string 22 fabricated of an insulation fiber material such as nylon or polyester is inserted inside an electro-conductive thread used as the transmission line 104. A narrow width fabric is made of an insulation thread by inserting an end of the string having one or more threads inside the electro-conductive thread.

This method of insulating prevents metal from minutely dropping due to friction with a fabric material or skin caused by motion of a human body, thereby solving problems stemming from the use of metal threads. In order to attach the connector 21 which connects the narrow width fabric with the physiological signal measuring unit 30, the electro-conductive thread constituting the narrow width fabric are spaced apart from each other by 2.54 mm.

To transmit a physiological signal to the physiological signal measuring unit 30 through the transmission line 104, the connecter 21 which connects the transmission line 104 with the physiological signal measuring unit 30 is attached to an end of the transmission line 104. The connecter 21 includes a contact which is connected to the transmission line 104 by an electro-conductive string 22 and a housing which is an external insulating material covering the contact.

As shown in FIG. 4, the transmission line 104 has a bulk shape because physiological signals are detected from several body portions, and are transmitted to the physiological signal measuring unit 30.

Figure 5:
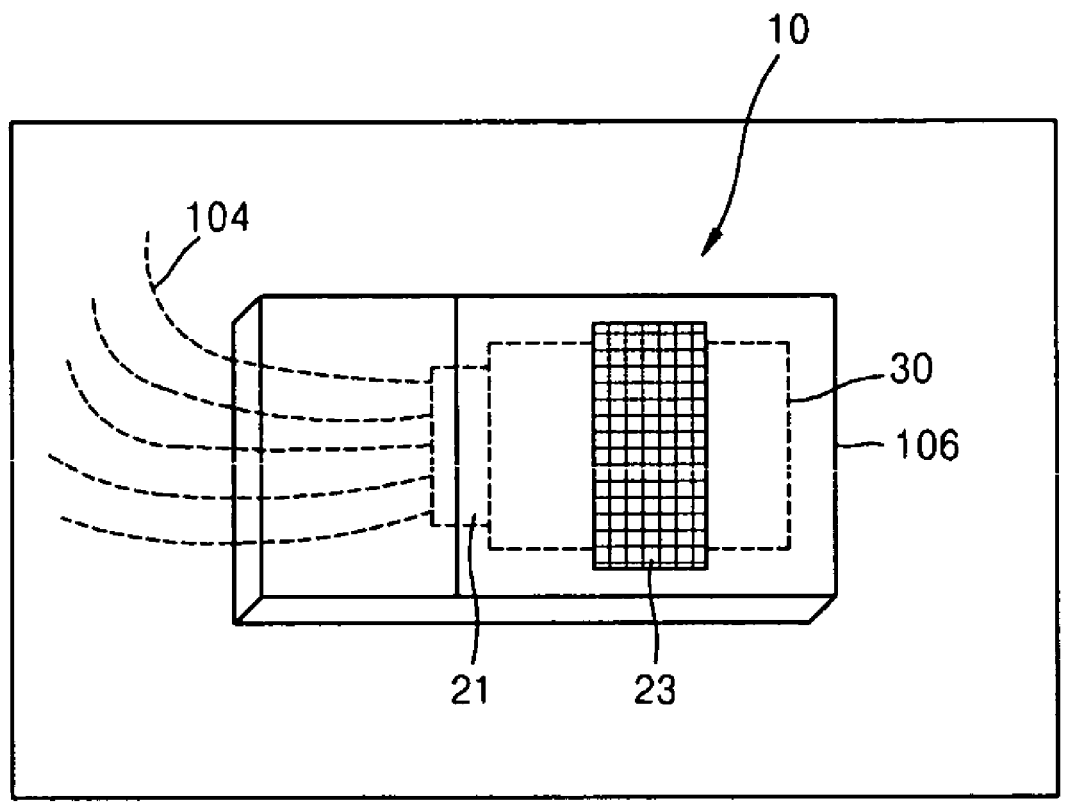
FIG. 5 is a front view of a pocket of FIG. 1 which is attached to an outer surface of a garment and can contain a physiological signal measuring unit.

FIG. 5 is a front view of a pocket of FIG. 1 which is attached to an outer surface of a garment and can contain a physiological signal measuring unit. The physiological signal measuring unit 30 may be fixed by using an elastic fabric material, or a Velcro band 23 inside a pocket 106. Since the physiological signal measuring unit 30 is fixed, normal motion does not affect its operation.

Figure 6:
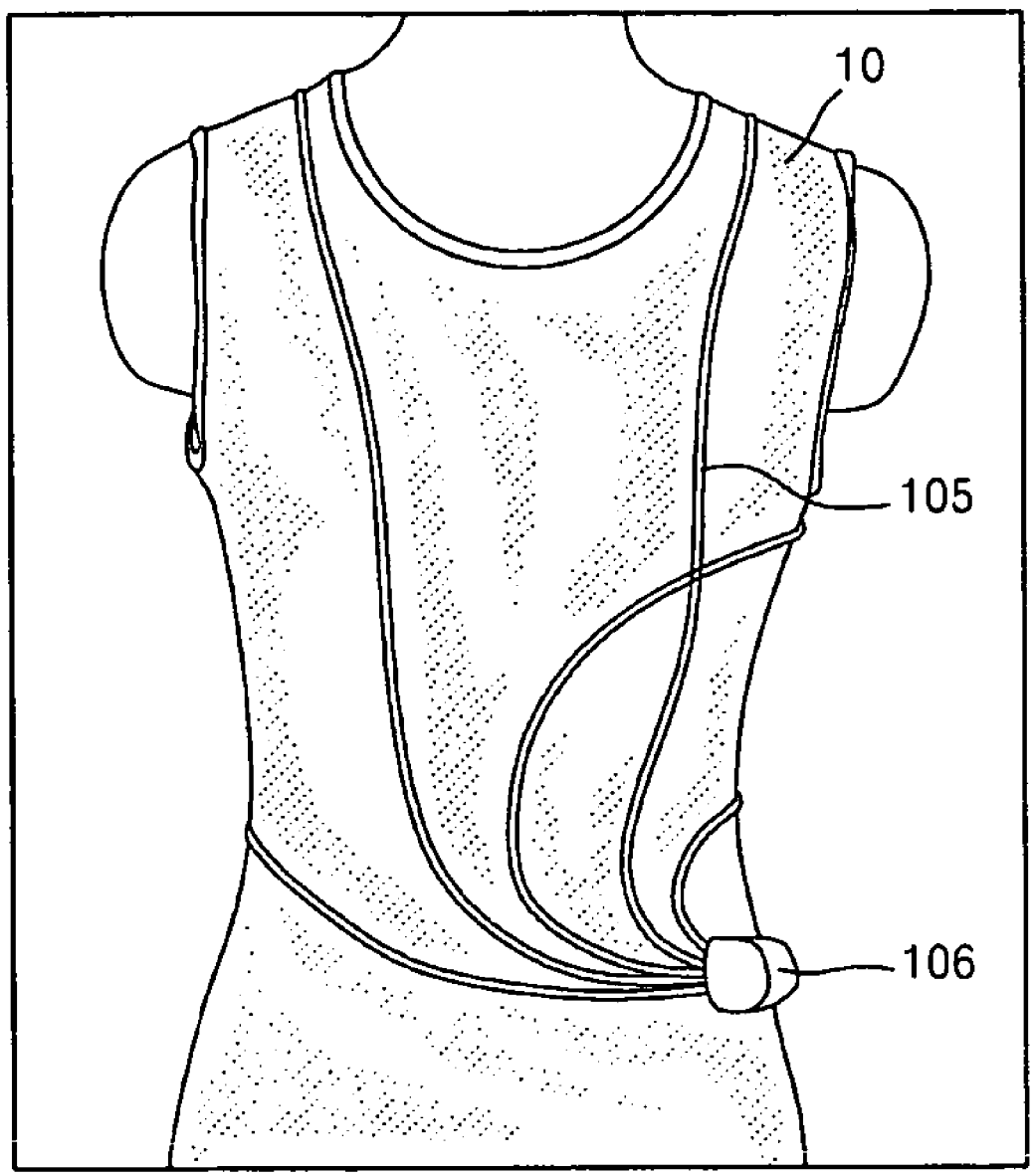
FIG. 6 illustrates a smart garment which is used for measuring a physiological signal and is dressed on a mannequin.

FIG. 6 illustrates a smart garment which is used for measuring a physiological signal and is dressed on a mannequin. The garment does not look different from a normal dress. Furthermore, an aesthetic effect of the garment 10 can be emphasized by a curved line of the tuck 105 and by a disposition of the pocket 106.

Figure 7:
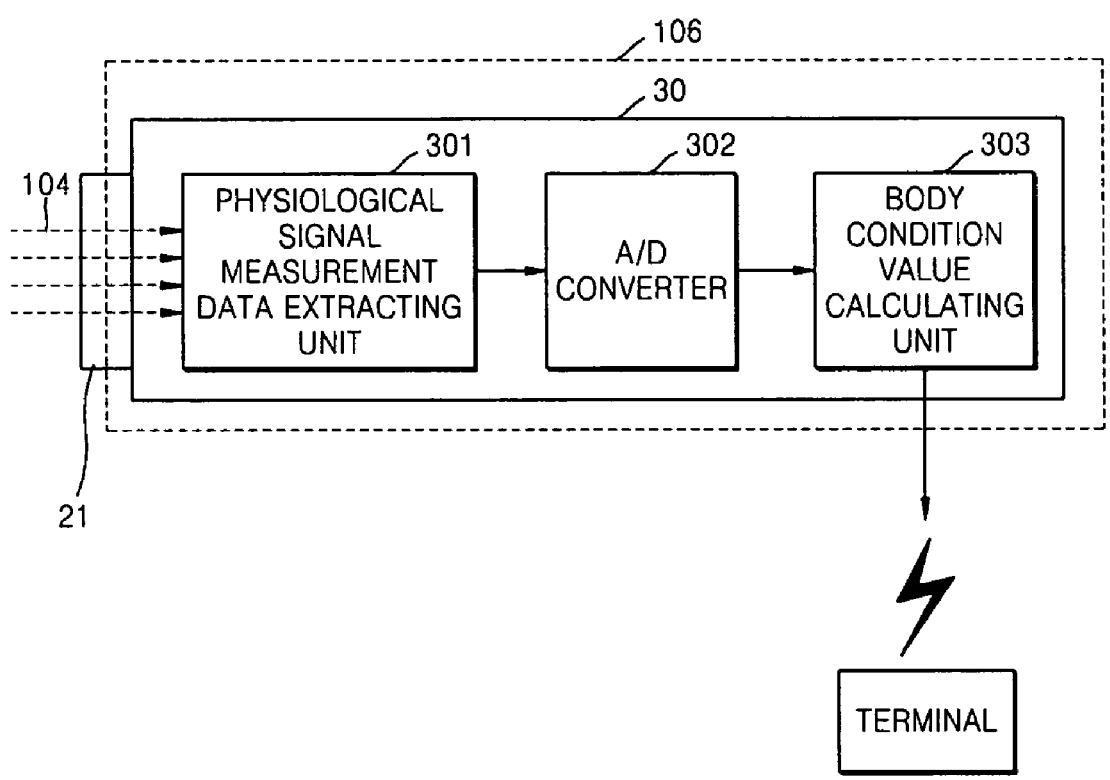
FIG. 7 illustrates a way of communication between a physiological signal measuring unit and an external terminal according to an embodiment of the present invention.

FIG. 7 illustrates a way of communication between a physiological signal measuring unit and an external terminal according to an embodiment of the present invention.

A physiological signal measurement data extracting unit 301 extracts analog data such as electrocardiogram, breathing, acceleration, and temperature data from a physiological signal transmitted through the transmission line 104. Here, since the transmitted physiological signal has an extremely low amplitude, the physiological signal has to be amplified in order to be measured. For this reason, the physiological signal measurement data extracting unit 301 includes an amplifying circuit, and the analog data is extracted after the transmitted physiological signal is amplified to have a sufficient intensity to be detected.

The A/D converter 302 converts the extracted analog data into digital data. A body condition value calculating unit 303 calculates a body condition value (e.g. heart rate, respiratory rate, quantity of motion, distance of motion, calories, or body temperature) from the digital data, and transmits the body condition value to the external terminal by wire or wireless transmission.

Although it has been described that data regarding electrocardiogram, breathing, acceleration, and temperature are processed in the present invention, a circuit for detecting other physiological signals such as blood pressure and oxygen saturation may be additionally provided. When the electrocardiogram, breathing, acceleration, and temperature need to be separately monitored for a specified monitoring group, the circuit for detecting other physiological signals may be removed.

According to the present invention, a physiological signal can be detected by attaching an electrode to an inner surface of a normal garment, and noise that may produced due to motion of a user can be removed by coating the electrode with an adhesive silicon. In addition, a tuck is formed in the garment, a physiological signal transmission line is inserted therein, and the tuck is sewn forming a curved line so that the transmission line with non-elongation can cope with elongation and bending of the garment, thereby achieving a wearable garment. In addition, the transmission line is insulated by using an insulation thread, to transmit the physiological signal in a safe manner.

An apparatus combined with a garment for detecting a physiological signal and wirelessly transmitting data of a measured physiological signal can monitor the physiological signal while an electrode can maintain a stable contact with skin in everyday life. As a result, the physiological signal can be monitored for a long time, and thus a current health condition can be checked and stored in a database, thereby achieving systematical health management and disease protection. In addition, changes in the physiological signal can be analyzed according to an exercise load, so that athletes can improve their athletic ability. Furthermore, workers exposed to highly dangerous conditions, for example, firefighters, policemen, and military personnel, may wear the garment so that emergency situations can be monitored for saving a life.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A smart garment for measuring physiological signals, comprising:
   a garment configured to cover the chest of a person,
   wherein the garment has a first and second side comprising:
      an electrode which is made of an electro-conductive fabric and detects a physiological signal, which is attached to the second side of the garment so as to be between the skin of the person and the second side of the garment during use;
      a physiological signal transmission line having a first and second end,
      wherein the first end is connected to the electro-conductive fabric through which the detected physiological signal is transmitted;
      a physiological signal measuring unit which is connected to the second end of the transmission line, receives the physiological signal, and measures information regarding body conditions related to the physiological signal,
      wherein the physiological signal transmission line is made of an electro-conductive thread; and
      a pocket where the physiological signal measuring unit is inserted,
      wherein a curved tuck is formed on the first side of the garment, and the physiological signal transmission line is inserted inside the tuck, so that the transmission line is insulated, and the transmission line without elongation can easily cope with elongation and bending of a garment material,
   wherein the curved tuck is formed such that the transmission line can be disposed in any position on the first side of the garment,
   wherein the tuck is formed by folding and sewing the garment,
   wherein the physiological signal transmission line is insulated by a fiber material inserted inside the electro-conductive thread, which is made of insulation thread from a narrow width fabric by inserting an end of a string having one or more threads inside the electro-conductive thread, and
   wherein the string is fabricated of the insulation fiber material.

2. The smart garment of claim 1, wherein an adhesive silicon is coated around the electrode to reduce a contact resistance between the electrode and skin of a user, so as to reduce noise generated when the electrode detects the physiological signal.

3. The smart garment of claim 1, wherein when the garment is made of a non-elastic material, a surface of the garment is insulated by using a heat-fusion tape or adhesive used for seam sealing.

4. The smart garment of claim 1, wherein a hook and loop fastener is included inside the pocket, and the physiological signal measuring unit is fixed to the pocket by the hook and loop fastener.

5. The smart garment of claim 1, wherein the physiological signal measuring unit is fixed by using an elastic fabric as a material of the pocket.

6. The smart garment of claim 1, wherein the physiological signal measuring unit comprises:
   a physiological signal measurement data extracting unit which extracts data after the received physiological signal is amplified; and
   a body condition value calculating unit which calculates a body condition value from the extracted data, and transmits the body condition value to an external terminal by wire or wirelessly.

* * * * *